United States Patent [19]

Hutchins

[11] Patent Number: 4,583,524
[45] Date of Patent: Apr. 22, 1986

[54] CARDIOPULMONARY RESUSCITATION PROMPTING

[76] Inventor: Donald C. Hutchins, 60 Brookdale Dr., Springfield, Mass. 01104

[21] Appl. No.: 673,838

[22] Filed: Nov. 21, 1984

[51] Int. Cl.$^4$ .............................................. A61B 19/00
[52] U.S. Cl. ................................... 128/1 R; 434/262
[58] Field of Search ............ 128/1 R, 630, 695, 696; 434/227, 228, 230, 262, 265; 381/51

[56] References Cited

U.S. PATENT DOCUMENTS

| | | | |
|---|---|---|---|
| 3,520,071 | 7/1970 | Abrahamson et al. | 434/265 |
| 4,016,540 | 4/1977 | Hyatt | 381/51 |
| 4,023,276 | 5/1977 | Furukawa et al. | 128/696 |
| 4,101,883 | 7/1978 | Hempenius et al. | 128/668 |
| 4,360,345 | 11/1982 | Hon | 434/262 |
| 4,370,983 | 2/1983 | Lichtenstein | 128/630 |
| 4,420,813 | 12/1983 | Inoue et al. | 381/51 |
| 4,457,312 | 7/1984 | Ornato et al. | 128/711 |
| 4,472,146 | 9/1984 | Weissbrod | 434/262 |
| 4,489,387 | 12/1984 | Lamb et al. | 128/630 |
| 4,510,942 | 4/1985 | Miyamae et al. | 128/683 |

FOREIGN PATENT DOCUMENTS

8418   1/1982   Japan .................................. 128/710

*Primary Examiner*—William E. Kamm
*Attorney, Agent, or Firm*—Charles Hieken

[57] ABSTRACT

A portable self-powered electronic cardiopulmonary resuscitation prompting system includes a keyboard on the front panel for turning the apparatus on, identifying the nature of the victim, the number of rescuers, whether mouth-to-mouth resuscitation is to be given and whether the victim is conscious or unconscious. The cabinet also includes an LCD display for furnishing visual information to the rescuer and a loudspeaker for providing audible intelligible prompts that are reproduced phonemes originating with a speech synthesizer LSI chip using the PARCOR method in response to signals provided by a microcomputer that processes the information indicated by the keyboard entries.

8 Claims, 7 Drawing Figures

CARDIOPULMONARY RESUSCITATION PROMPTING

The present invention relates in general to cardiopulmonary resuscitation and more particularly concerns novel apparatus and techniques for prompting one or more rescuers to properly follow rescue procedures, such as prescribed by the American Heart Association in conjunction with the American Red Cross, with apparatus that is relatively easy to operate by relatively unskilled personnel to provide major assistance during emergency conditions requiring CPR efforts by nonmedical personnel.

These procedures are based on information provided by the Division of Medical Science, National Academy of Sciences, National Research Council.

Cardiopulmonary Resuscitation, also known as CPR, is a combination of artificial respiration and artificial circulation, which should be started as an emergency procedure when cardiac arrest occurs by those properly trained to do so.

To understand the principles and techniques of cardiopulmonary resuscitation, it is important to know some of the concepts involved in this procedure.

The following points are important to remember:

1. Air that enters the lungs contains about 21 percent oxygen and only a trace of carbon dioxide. Air that is exhaled from the lungs contains about 16 percent oxygen and 4 percent carbon dioxide.

2. The right side of the heart pumps blood to the lungs where the blood picks up oxygen and releases carbon dioxide.

3. The oxygenated blood then returns to the left side of the heart, from where it is pumped to the tissues of the body.

4. In the body tissues, the blood releases oxygen and takes up carbon dioxide, after which it flows back to the right side of the heart.

5. All body tissues require oxygen, but the brain requires more than any other tissue. It is generally estimated that if the brain is totally deprived of oxygenated blood for a period of four to six minutes, it will probably suffer irreversible damage.

6. The condition that exists when breathing and circulation stop is called clinical death.

7. The condition that exists when the brain has been deprived of oxygenated blood for a period of six minutes or more and irreversible damage has probably occurred is called biological death.

Both ventilation and circulation are required to maintain life.

When breathing stops, the circulation and pulse may continue for some time, a condition known as respiratory arrest. In this case, only artificial respiration is required, since the heart action continues to circulate blood to the brain and the rest of the body. Common causes of respiratory arrest are drowning, electric shock, suffocation, strangulation, accidents and drug overdosage.

When circulation stops, the pulse disappears and breathing stops at the same time or soon thereafter. This condition is known as cardiac arrest. When cardiac arrest occurs, both artificial respiration and artificial circulation are required to oxygenate the blood and circulate it to the brain. Common causes of cardiac arrest are heart attack; electric shock; hemorrhage; and, as a final phase of drowning, suffocation and other forms of respiratory arrest.

There are some situations which require special actions for the artificial resuscitation; one of these is choking. It is during eating that obstruction of the airway by foreign bodies most often occurs. In adults, meat is the most common object that causes obstruction; but, in children, and in some adults, a variety of other foods and foreign bodies may lead to a blockage of the airway.

A number of years ago, the American Red Cross (ARC) and the American Heart Association (AHA) developed a Statement of Cooperation between the two organizations. Under this Agreement, AHA assumed the role of research and ARC developed instruction programs in CPR to train nonprofessional rescuers. Under these programs, millions have been trained and thousands of lives have been saved.

To be certified as a CPR rescuer, a person is taught a series of physical procedures that cause artificial breathing and circulation. These procedures, such as chest thrusts, are called for in prescribed sequences and with specific timing. The sequence and timing are important because they are directly related to a standard pulse beat needed to prevent biological death.

U.S. authorities have agreed upon a method of CPR. For training purposes, most instructors furnish the *Red Cross CPR Module*, the standard for CPR training in the United States.

CPR procedures differ depending upon the condition and age of the victim and also the number of trained CPR rescuers present. For example, in a one rescuer situation, the *Module* asks for a rate of 80 compressions per minute for an adult and 100 compressions per minute for a child. With two rescuer CPR, 60 compressions per minute is required.

These cycles are interrupted at specified intervals when diagnoses of vital signs are required and when a different breathing pattern is needed. While all these directions burden the rescuer's mind, he must remember such important steps as: "Keep the airway passage open," "Check for pulse," "Seal off the nose," "Tilt the head back," and other steps.

The single biggest challenge remaining in CPR training is to find a solution to the problem of skill and knowledge decay. The Red Cross has promoted recertification classes each year after the initial course, and this has been a partial solution to this problem. However, in reality, only a small percentage attend these recertification classes. As a result, millions of people trained in CPR are rusty when it comes to instant recall of the routines, timing, and sequence of actions.

There are also those who have the knowledge but who panic or go blank under the stress of an emergency. It is one thing to have the knowledge and something quite different to recall and follow correct procedures when a loved one is unconscious, lifeless, or choking.

Various methods of prompting have been promoted, yet all established solutions have flaws which limit their success. One idea is a simple wallet size card that those trained in CPR can carry and read. Unfortunately, the small size of the cards limits the number of instructions they can carry and the rescuer must divert his attention from the victim to read the prompts.

Audio instruction tapes, while useful in the classroom, are of little or no help in emergencies. Tapes are recorded sequentially and tape recorders lack the search techniques needed to find and produce the proper instruction sequence demanded for a particular situation.

Telephone "hot lines" have been used experimentally in some cities. Generally when monies from the funding grants have dried up, the CPR "hot lines" have closed down.

Emergency Medical Technicians have made good use of two-way radio and cable networks. When patched into hospital facilities, both instructions and diagnostic information can be transmitted. Unfortunately, a victim of cardiac arrest has only 4 minutes before brain damage is probable. In most of these cases, professional help arrives too late. The need is for immediate attention from a CPR trained bystander.

It is therefore an object of this invention to provide a portable device to provide prompts to those previously trained in CPR, preferably capable of moving to and with the victim.

Another object is to prompt with audio sounds or voice to allow the rescuer free use of his hands, eyes, voice, mouth, and body.

A third object is to be public-utility independent with no reliance on telephone lines, A.C. electric outlets, or radio and cable circuits.

A fourth object of this invention is to employ conventional technology so that the device is relatively inexpensive to manufacture, maintain, and use. This low cost helps insure that the invention will be just as available and prominent in public buildings as fire extinguishers and smoke detectors.

A fifth object is to provide an instrument which is simple to understand and easy for one rescuer to operate.

A sixth object is to offer the user either keypad, menu, or punch-button input to initiate one of several CPR procedures published in the *Red Cross CPR Module.*

A seventh object of this invention is to give the rescuer accurate timing for each CPR maneuver.

An eighth object is to give the rescuer the proper count of repetitions in breathing and thrust routines.

A ninth object of the invention is to offer the rescuer calm, accurate instructions which will build confidence and lend encouragement to counteract the stress of emergencies.

A tenth object is to provide for easy logic changes should the instructions provided by the *Red Cross CPR Module* change in the future.

An eleventh object of this invention is to make provision for access ports to allow diagnostic enhancements in the future, such as direct pulse reading devices and output ports for modems.

A twelfth object is to enable the rescuer to quickly change the CPR prompts should the condition of the victim change or should another rescuer appear on the scene to help.

A thirteenth object of this invention is to allow for international availability and use, being capable of supporting different languages.

In addition to its use in the field, the invention may be of special value in the schooling and recertification of rescuers, especially in that while it demonstrates the necessary rescue procedures, it offers perfect timing for the trainee. Instruction varies with regard to accurate timing for most CPR courses.

These and other objects of the invention are achieved with apparatus which allows electronic microcircuit logic to output audio instructions that can be heard by the rescuer. The sound for these instructions is preferably created and broadcast by using an electronic voice synthesizer, speech chip, amplifier, and speaker or any other electronic device which produces sound as prompts that can be understood and executed by a CPR rescuer.

Numerous other features, objects and advantages of the invention will become apparent from the following specification when read in connection with the accompanying drawing in which.

Figure 1:
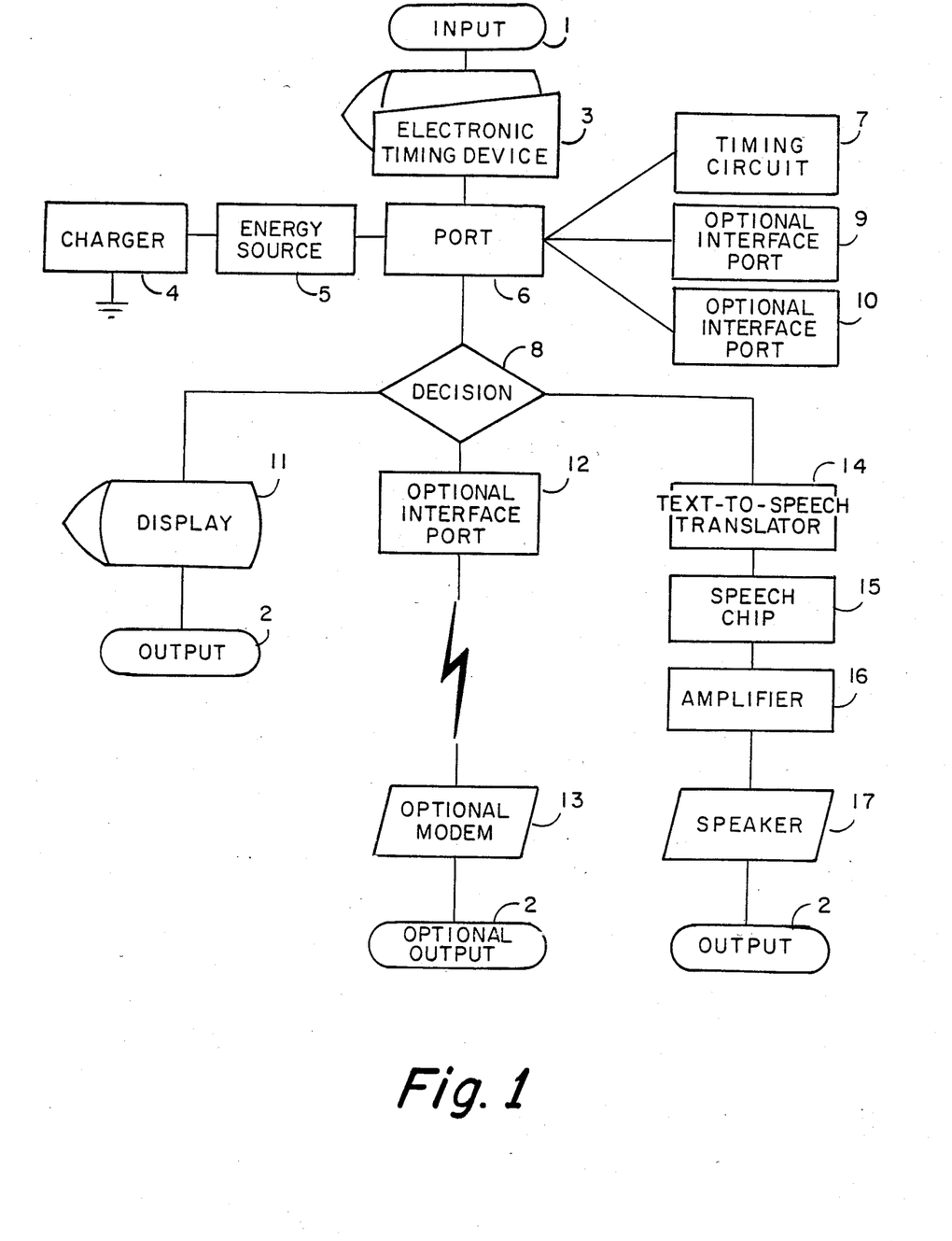
FIG. 1 is a block diagram illustrating the logical arrangement of a system according to the invention.

With reference now to the drawing and more particularly FIG. 1 thereof, there is shown a block diagram illustrating the logical arrangement of a system according to the invention. The invention includes an electronic input device 3, preferably a keypad or key button for manual startup, test circuits, and program selection. Batteries or a light sensitive energizer 5 may provide electric power to allow portability. If energizer 5 comprises batteries, a plug type A.C. charger 4 may charge them to insure that the batteries are fully charged when needed.

The central processing unit 6 may comprise a solid-state device programmed with the logic necessary to prompt the CPR rescuer. This programmable unit may comprise an electronic chip or series of chips that provide repetition counters, conditional responses, buffer storage, and output formats required. Timing circuit 7 may provide a "clock" for timing the CPR procedures.

Some output signals may be used to "print" words or characters on a display 11 typically comprising DRO's or LCD's.

Other output signals energize "Voice Synthesizer Circuitry," comprising: text to speech translator 14; speech chip 15; amplifier 16; and audio output speaker 17. There are many methods of speech synthesis such as phoneme, LPC (Linear-Predictive Coding), DPCM (Differential Pulse-Code Modulation), and ADPCM (Adaptive Differential Pulse-Code Modulation). While FIG. 1 shows an analysis-synthesis technique, any other method furnishing understandable speech is suitable. For the preferred embodiment of the invention, study has shown when an analysis-synthesis system is fabricated on a silicon chip, it offers long speech times at low cost. Using this PARCOR system, speech signal waveforms are analyzed and specific parameters are encoded in the forms of digital data, and decoded from the data for synthesis. This system has the advantage of requiring far less data memory because data is compressed through analysis and encoding. Voice output can also be constructed in languages other than English to allow international use of the invention.

Peripheral devices 9, 10 and 12 may include means for diagnosis of the victim or other desirable functions.

An analog type blood pressure and pulse rate reader may provide signals representative of blood pressure and heart rate into the CPU logic through interface ports 9 and 10.

Interface port 12 may provide output signals for diagnostic display and communication through a modem to medical professionals involved in a community emergency medical services (EMS) System.

Figure 2:
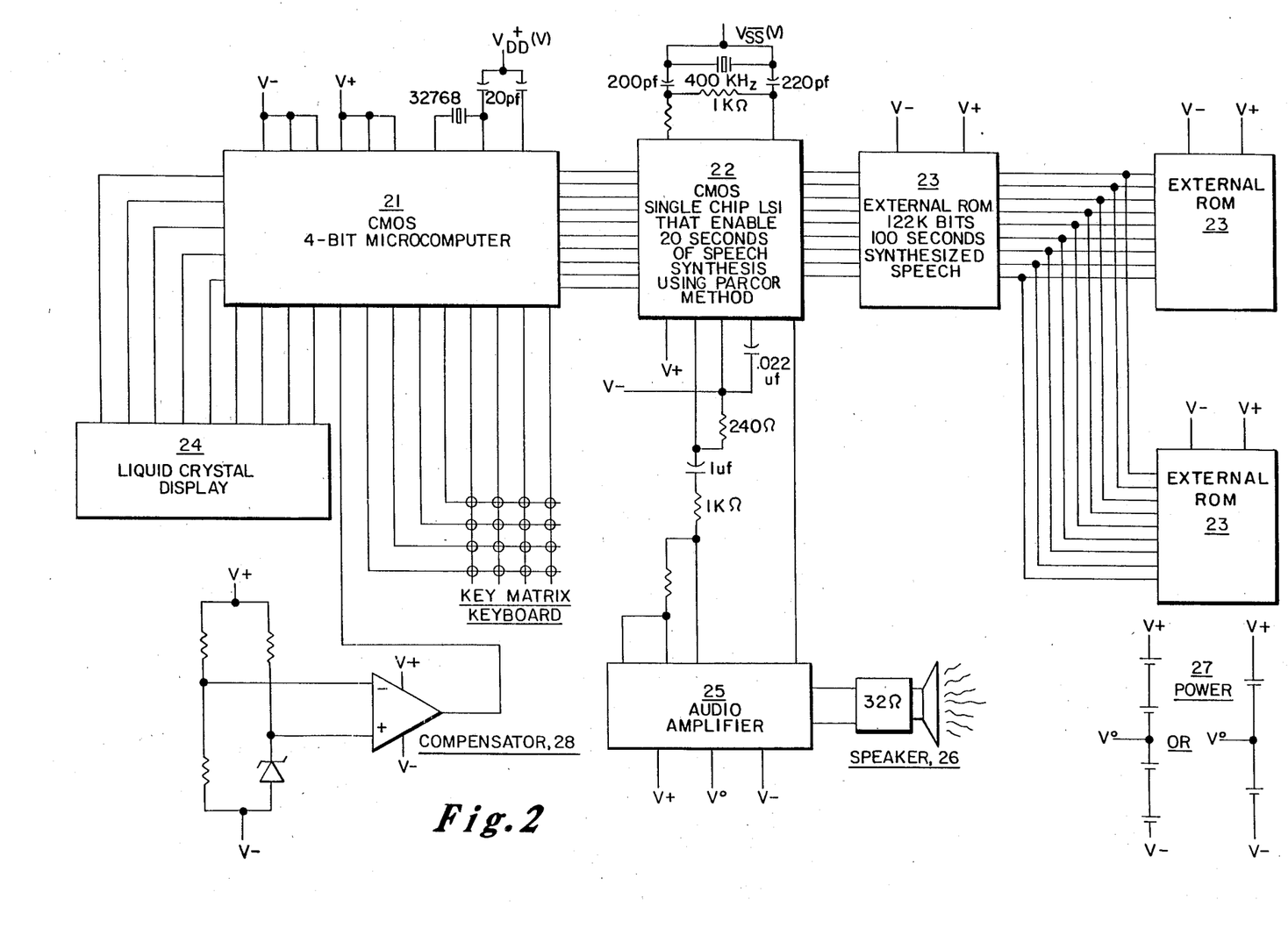
FIG. 2 is a combined block schematic-circuit diagram of an exemplary embodiment of the invention.

Referring to FIG. 2, there is shown a combined block-schematic diagram illustrating the logical arrangement of components in a system according to the invention. The system includes a CMOS 4-bit microcomputer, such as a Sanyo Electric Co. LTD LC 5800 CMOS LSI with LCS driver, that operates on low voltage, very small current and includes an LCD driver, a 4-bit parallel processing arithmetic logic unit, a plurality of LCD segment outputs, input/output ports, a prescaler and a 32.768 kHz crystal oscillator.

Microcomputer 21 provides signals to LSICMOS single chip speech synthesizer 22 that may provide up to 20 seconds of synthesized speech using the known PARCOR method.

Synthesizer 22 may deliver these segments to external ROM capable of storing 128K bits of information to store 100 seconds of buffered synthesized speech signals.

LCD 24 may display graphically the specific key that has been pressed by an operator and also display messages to a rescuer in alphanumeric form.

LSICMOS single chip audio amplifier 25 amplifies the synthesized speech signals provided by synthesizer 22 and energizes loudspeaker 26 with intelligible sounds used by the rescuer that may represent both voiced sounds with instructions and beats for insuring proper timing of victim-assistance maneuvers.

Figure 3:
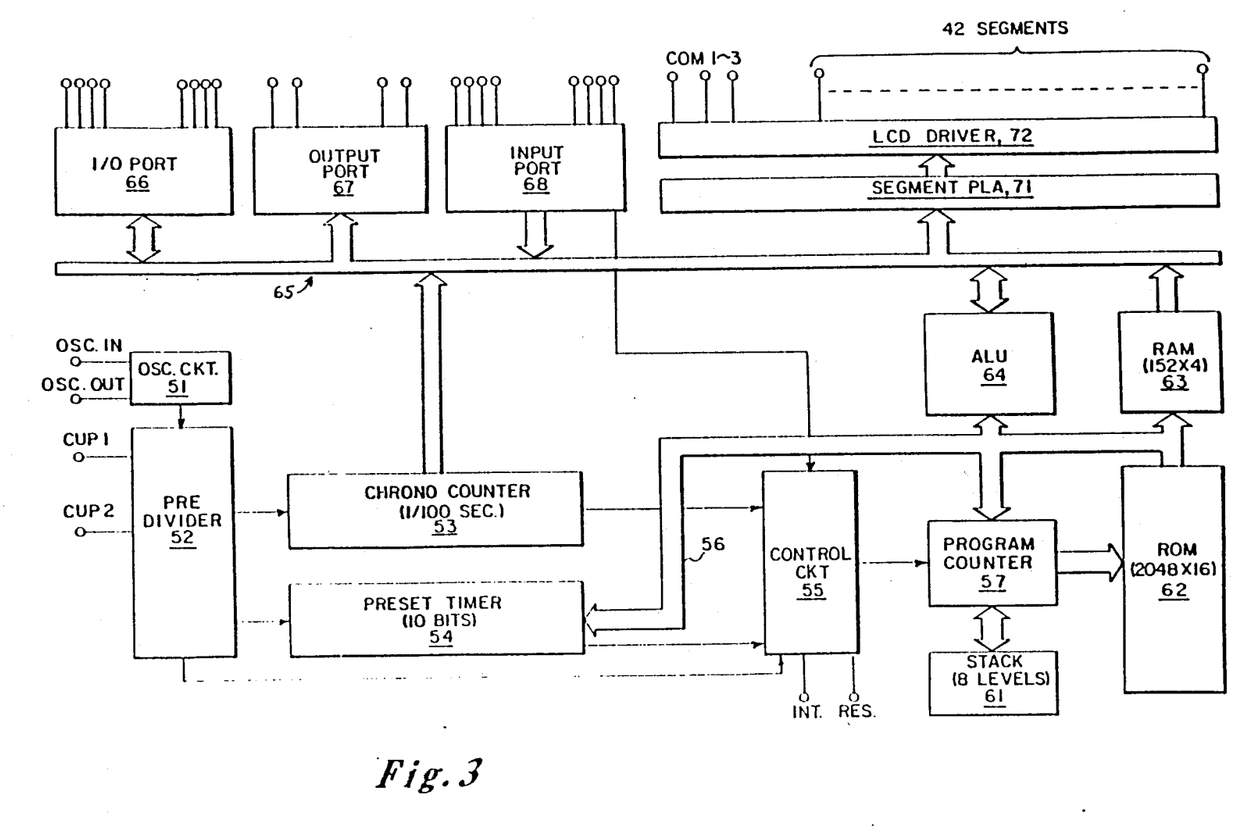
FIG. 3 is a block diagram illustrating the logical arrangement of an embodiment of the invention showing timing signals.

Referring to FIG. 3, there is shown a block diagram illustrating the logical arrangement of CMOS 4-bit microcomputer 21. This unit, which is a commercially available LSI (Sanyo Electric Co. Ltd. #LC5800 C MOS LSI, with LCD Driver), typically comprises an oscillator circuit 51 that energizes a predivider 52. Predivider 52 energizes a chrono counter 53 with a pulse every 1/100 second and preset timer 54 with clock pulses to produce a carry pulse when reset to zero to control circuit 55. Control circuit 55 also receives timing signals from chrono counter 53 and appropriate signals from bus 56.

Control circuit 55 also energizes program counter 57 that may exchange data with bus 56, 8-level memory stack 61, and read only memory 62.

Read only memory 62, random access memory 63 and arithimetic logic unit 64 also communicate with bus 56. Arithimetic logic unit 64 and random access memory 63 also communicate with bus 65 that also links I/O port 66, output port 67, input port 68 and segment programmable logic array 71 that energizes LCD driver 72.

Figure 4:
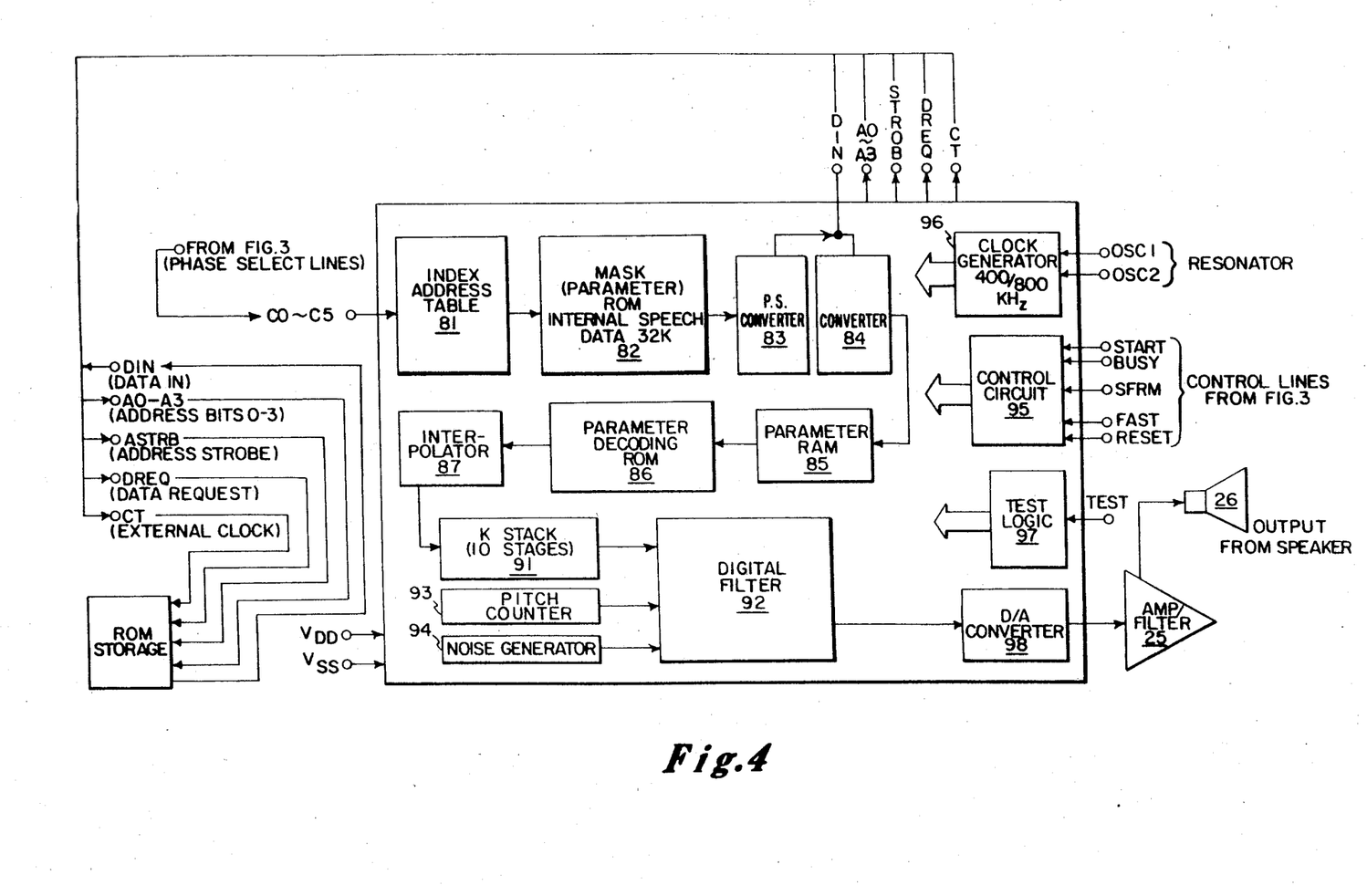
FIG. 4 is a block diagram illustrating the logical arrangement of voice synthesizing elements.

Referring to FIG. 4, there is shown a block diagram illustrating the logical arrangement of CMOS, LSI single chip speech synthesizer 22, which typically may be a (Sanyo Electric Co. #LC8100 C MOS LSI), integrated circuit in association with audio amplifier 25 and loudspeaker 26. This chip typically comprises an index address table read only memory 81 for specifying the indexed address for words to be generated with the C0 and C5 code and a masked parameter read only memory 82 to store speech parameters. Memory 82 energizes a parallel-serial converter 83 that energizes a converter 84 that may also receive a signal on the DIN input to energize a parameter random access memory 85, to store parameters or one frame, that provides a signal to parameter read only memory 86. Memory 86, which is used to decode parameters non-linearly, energizes interpolator 87 to provide signals to K stack 91, typically of 10 stages. K stack 91 energizes digital filter 92 that also receives signals from pitch counter 93 and noise generator 94, the voiced and unvoiced sound sources, to provide digital representations of the selected words that are converted by digital-to-analog converter 98 to voiced signals amplified to power amplifier 25 and reproduced by loudspeaker 26. Chip 22 also includes test logic 97, control circuitry 95 and 400/800 kHz clock generator 96 for providing clock pulses.

Figure 5:
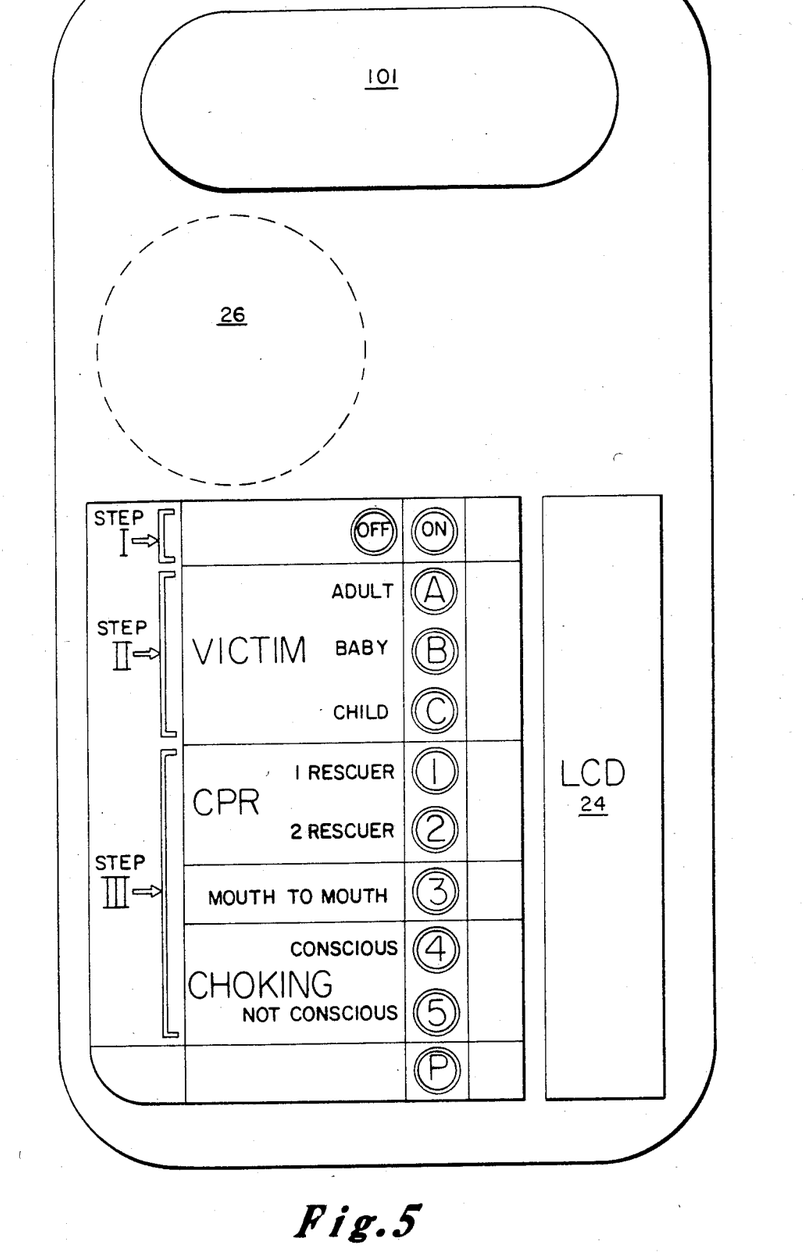
FIG. 5 is a front view of a preferred form of cabinet according to the invention showing the simplified keyboard.

Referring to FIG. 5, there is shown a preferred form of the front panel of the instrument illustrating the various steps and the preferred form of keyboard. The case is formed with a handle 101 to permit convenient carrying and includes keys designated off, on, A, B, C, 1–5 and P. LCD display 24 displays appropriate visual information as indicated above, and loudspeaker 26 provides appropriate aural information.

Step I involves pressing the ON button. Step II involves pressing one of buttons A, B or C to identify whether the victim to be treated is an adult, baby or child, respectively. Steps III involves pressing one of buttons 1 or 2 to indicate whether 1 or 2 rescuers, respectively, are available for treatment, pressing button 3 to indicate that mouth-to-mouth artificial respiration will be given, and pressing one of buttons 4 or 5 to indicate whether the choking victim is conscious or not conscious. Pressing the P or pause key causes the apparatus to pause in providing prompts until the rescuer is ready.

Figure 6:
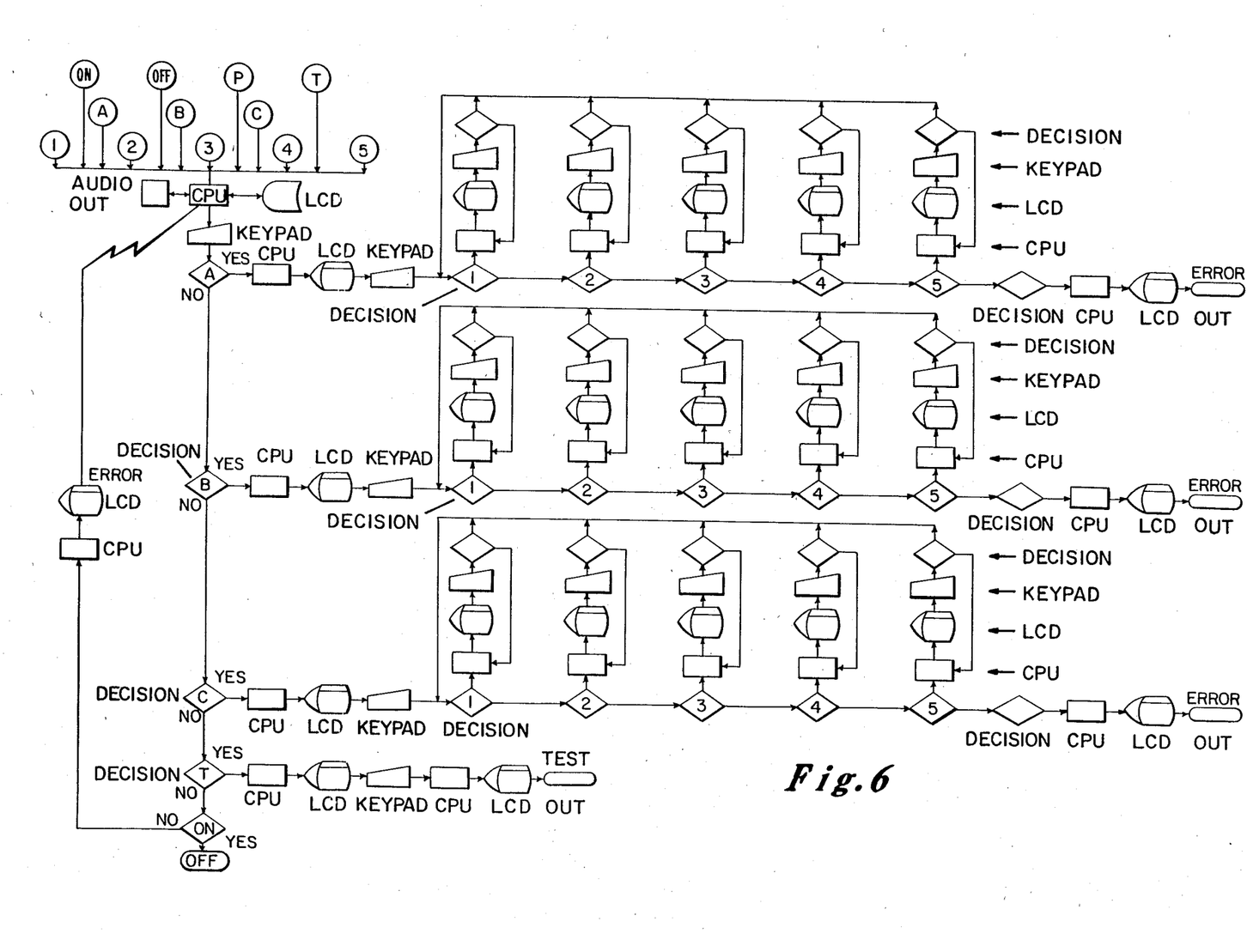
FIG. 6 is a logical diagram illustrating the steps in a program for practicing the invention.
Figure 7:
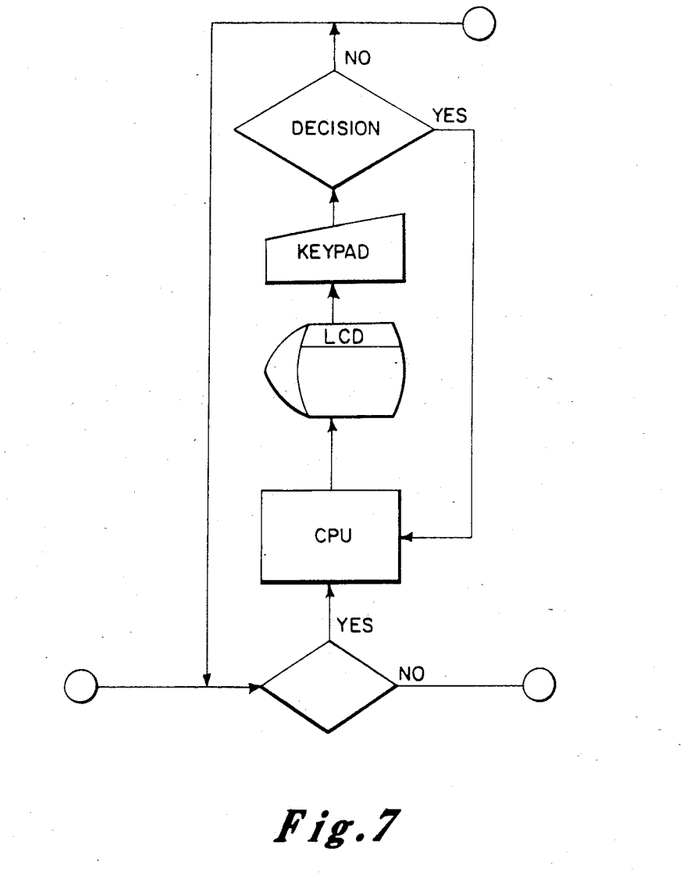
FIG. 7 illustrates the logical arrangement for carrying out steps in the program.

Referring to FIG. 6, there is shown logical diagrams illustrating the steps in the process according to the invention in symbolic logic. FIG. 7 illustrates a detail of the subroutine according to the invention. The diamond-shaped boxes represent a decision, the trapezoidal boxes represent a keypad condition, the barrel-shaped boxes represent output displays, and the rectangular boxes represent CPU processing. The process will be better understood by considering the following example in the decision tree of FIG. 6.

With reference again to FIG. 5, the invention disclosed has the following Key Matrix. The "on" Key prompts the initial decision on which the rescuer must take action; Is the victim Adult, Baby or Child, (A, B or C)? This response, when keyed, leads the rescuer through a series of emergency techniques and then asks for a decision on the rescuer's diagnosis of the victim's condition and the rescue procedure required. The choices are:

1. One Rescuer CPR
2. Two Rescuer CPR
3. Mouth-to-Mouth Breathing
4. Choking—Victim Conscious
5. Choking—Victim Not Conscious Once the rescuer decides on the "Age Logic Path," (A, B or C), the program stays with this path until the invention is restarted. If the condition of the victim changes or another rescuer joins the first rescuer, the rescuer can instantly change the logic path with keys 1, 2, 3, 4 and 5 in accordance with the new requirement.

The logic for the preferred embodiment also includes provision for error messages and a pause key.

The operation of the apparatus will now be discussed with reference again to FIG. 1. When a person trained in CPR is confronted with an unconscious or choking victim, he or she immediately checks vital signs and calls for help. The rescuer then locates the invention, which should be found in numerous places much like a fire extinguisher. The invention is light and portable because of battery power, integrated circuits and a small case. The rescuer turns on the invention and listens for the prompts that will help diagnose the victim and initiate CPR.

After diagnosing the condition and ages of the victim, the rescuer selects one of several logic paths through the input module 3. The choice might be such classifications as: Single rescuer/multi-rescuer; Infant/child/adult; Choking/not choking; for example. The rescuer would then hear voice commands as output from the I.C. logic and perform the tasks as directed. The number of CPR repetitions would be accurate because the CPU logic would do the counting. The timing would be perfect for the same reason. Prompts would be heard at the proper time for diagnostic checks of breathing, pulse, and other conditions.

If the condition of the victim changed, i.e. from "no pulse" to "pulse OK," the rescuer could key in this new information which would allow the central processing unit to rapidly search and select a new logic path. Should a second rescuer come upon the scene to help, again the logic path can be quickly changed with a keystroke.

The invention shows no fatigue (an electronic chip has no moving parts). It performs calmly and faithfully until it is intentionally stopped or until the batteries wear down. It outlasts the stamina of most rescuers. The power consumption of these LSI chips is very low when operating. The built-in power standby modes may draw negligible power when not in use. For this reason simple AA size batteries may power this device for extremely long periods of time. The low power requirements of the LCD as compared to other display technology will also be beneficial.

There has been described novel apparatus and techniques for providing CPR prompting to allow a person who has received training in CPR to properly perform it under emergency conditions with relatively compact, inexpensive, reliable apparatus. It is evident that those skilled in the art may now make numerous uses and modifications of and departures from the specific embodiments described herein without departing from the inventive concepts. Consequently, the invention is to be construed as embracing each and every novel feature and novel combination of features present in or possessed by the apparatus and techniques herein disclosed and limited solely by the spirit and scope of the appended claims.

What is claimed is:

1. Cardiopulmonary resuscitation prompting apparatus for providing audible verbal guidance to rescue personnel trained in CPR under emergency conditions for aiding a victim requiring CPR techniques comprising, keying means for entering information signals representative at least of characteristics of said victim and the number of said rescue personnel relevant to proper performance of cardiopulmonary resuscitation techniques, means responsive to the keyed information signals for providing output signals representative of proper steps to be taken in resuscitating said victim, and electroacoustical transducing means responsive to said output signals for providing audible intelligible sound signals representative of the proper resuscitation steps to be taken by said rescue personnel in resuscitating said victim.

2. Cardiopulmonary resuscitation prompting apparatus in accordance with claim 1 wherein said means responsive to the keyed information signals includes electronic speech synthesizing apparatus for providing voice signals identifying the cardiopulmonary resuscitation steps to be taken by said rescue personnel in resuscitating said victim.

3. Cardiopulmonary resuscitation prompting apparatus in accordance with claim 2 and further comprising circuit timing means for providing voice prompts at the exact time a particular cardiopulmonary resuscitation procedure step is to be taken by said rescue personnel in resuscitating said victim.

4. Cardiopulmonary resuscitation prompting apparatus in accordance with claim 1 and further comprising a portable case supporting said apparatus, said case also supporting a source of electrical energy for powering said apparatus, said case having a front panel, said keying means comprising a keyboard on said front panel including means for turning said apparatus on, means for identifying the nature of a victim, means for identifying the number of said rescue personnel, and means for identifying whether the victim is conscious or unconscious.

5. Cardiopulmonary resuscitation prompting apparatus in accordance with claim 1 wherein said case also includes an LCD display for furnishing visual information to the rescue personnel.

6. A method of cardiopulmonary resuscitation with cardiopulmonary resiscitation prompting apparatus for providing audible verbal guidance to rescue personnel trained in CPR under emergency conditions for aiding a victim requiring CPR techniques comprising, keying means for entering information signals relative to proper performance of cardiopulmonary resuscitation techniques, means responsive to the keyed information signals for providing output signals representative of proper steps to be taken in resuscitating a victim, and electroacoustical transducing means responsive to said output signals for providing audible intelligible sound signals representative of the proper resuscitation steps to be taken, which method includes the steps of, actuating said keying means to enter information signals representative at least of characteristics of said victim and the number of said rescue personnel relevant to proper performance of cardiopulmonary resuscitation techniques by said rescue personnel in resuscitating said victim, processing the keyed information signals to provide output signals representative of proper steps to be taken in resuscitating said victim, converting said output signals into audio signals corresponding to audible intelligible sound signals representative of the proper resuscitation steps to be taken by said rescue personnel in resuscitating said victim, and applying said audio signals to said electroacoustical transducing means to provide audible intelligible sound signals representative of the proper resuscitation steps to be taken by said rescue personnel in resuscitating said victim.

7. A method in accordance with claim 6 and further including the steps of, listening to said audible intelligible sound signals, and treating said victim in accordance with the audible intelligible sound signals provided by said electroacoustical transducing means.

8. A method in accordance with claim 6 wherein said audible intelligible sound signals include voice prompts at the exact time a particular cardiopulmonary resuscitation procedure step is to be taken, and taking the particular cardiopulmonary resuscitation procedure step associated with an identifying voice prompt at substantially the exact time such a voice prompt occurs.

* * * * *